(12) United States Patent
Bakor et al.

(10) Patent No.: US 11,821,823 B2
(45) Date of Patent: Nov. 21, 2023

(54) CREATING A HYDROGEN SULFIDE CRUDE OIL REFERENCE STANDARD

(71) Applicant: Saudi Arabian Oil Company, Dhahran (SA)

(72) Inventors: Radwan Bakor, Dammam (SA); Anas S. Rushaid, Khobar (SA)

(73) Assignee: Saudi Arabian Oil Company, Dhahran (SA)

( * ) Notice: Subject to any disclaimer, the term of this patent is extended or adjusted under 35 U.S.C. 154(b) by 186 days.

(21) Appl. No.: 17/391,689

(22) Filed: Aug. 2, 2021

(65) Prior Publication Data

US 2023/0035469 A1  Feb. 2, 2023

(51) Int. Cl.
*G01N 1/28* (2006.01)
*G01N 33/28* (2006.01)

(52) U.S. Cl.
CPC .............. *G01N 1/28* (2013.01); *G01N 33/287* (2013.01); *G01N 2001/2893* (2013.01)

(58) Field of Classification Search
CPC . G01N 1/28; G01N 33/287; G01N 2001/2893
See application file for complete search history.

(56) References Cited

U.S. PATENT DOCUMENTS

| 6,234,001 | B1 | 5/2001 | Sorensen et al. | |
| 6,319,722 | B1 | 11/2001 | Litwin et al. | |
| 6,997,347 | B2 | 2/2006 | Peng et al. | |
| 7,887,777 | B2 | 2/2011 | Wolfert et al. | |
| 8,518,706 | B2 | 8/2013 | Dessort et al. | |
| 2014/0004611 | A1* | 1/2014 | Feustel | G01N 33/287 436/60 |
| 2016/0061804 | A1* | 3/2016 | Chanbasha | G01N 30/14 73/61.61 |

OTHER PUBLICATIONS

ANSI/NACE Standard TM0284 (2003), Evaluation of Pipeline and Pressure Vessel Steels for Resistance to Hydrogen-Induced Cracking.
Zea et al., "Hydrogen Sulfide Absorption Phenomena in Brine/Oil Mixtures." SPE Journal 16.04, Dec. 2011, 931-939, 9 pages.

* cited by examiner

*Primary Examiner* — Cephia D Toomer
(74) *Attorney, Agent, or Firm* — Fish & Richardson P.C.

(57) ABSTRACT

A method and a system for creating a reference standard for hydrogen sulfide concentrations in crude oil are described. The method includes receiving a volume of crude oil in a vessel. A hydrogen sulfide gas is flowed from a pressurized gas cylinder to the vessel to form a hydrogen sulfide gas-crude oil mixture. The hydrogen sulfide gas continues to flow from the pressurized gas cylinder to the vessel at a set pressure for a predetermined time to adjust the hydrogen sulfide concentration in the hydrogen sulfide gas-crude oil mixture to a hydrogen sulfide threshold concentration. The flow of the hydrogen sulfide gas into the vessel is stopped.

8 Claims, 2 Drawing Sheets

CREATING A HYDROGEN SULFIDE CRUDE OIL REFERENCE STANDARD

TECHNICAL FIELD

This disclosure relates to performing an analysis of a chemical sample, in particular to creating a reference standard for a compound possibly present in a crude oil.

BACKGROUND

Tests can be performed on samples to determine a condition or a property of the samples. The tests can be performed by test instruments on the samples. Proper operation of the test instruments can be verified by performing the tests on samples with known conditions or known properties. Reference standards are samples with known conditions and properties.

SUMMARY

This disclosure describes system and methods related to creating a crude oil reference standard (e.g., a reference standard for hydrogen sulfide in crude oil). These systems and methods are discussed with respect to hydrogen sulfide but can also be used with other dissolved gas in crude oil.

These systems and methods provide an approach to creating crude oil reference standards for compounds that may be naturally present in the crude oil sample of interest. For example, dissolved hydrogen sulfide is sometimes present in crude oil from some fields in the Middle East. Exposing a sample of the crude oil to gas phase hydrogen sulfide at a set pressure and temperature for a set period of time can provide a controlled concentration of dissolved hydrogen sulfide in the sample. The initial sample of crude oil is first cleaned by bubbling the initial sample of crude oil with nitrogen gas to ensure the dissolved hydrogen sulfide concentration is less than 1 ppm. This avoids the requirement of an initially clean solvent in approaches that provide a reference standard by cleaning (by bubbling the nitrogen gas) and then spiking a known volume of solvent with a known volume of a compound of interest (e.g., hydrogen sulfide).

A reference standard for hydrogen sulfide concentrations in crude oil is created by receiving a volume of crude oil containing a dissolved gas (e.g., hydrogen sulfide) in a vessel. Hydrogen sulfide gas is flowed from a pressurized gas cylinder to the vessel to create a hydrogen sulfide gas-crude oil mixture. The hydrogen sulfide gas continues to flow from the pressurized gas cylinder to the vessel at a set pressure for a predetermined time to adjust the hydrogen sulfide concentration in the hydrogen sulfide gas-crude oil mixture to a hydrogen sulfide threshold concentration. Once the hydrogen sulfide concentration in the hydrogen sulfide gas-crude oil mixture is at the hydrogen sulfide threshold concentration, the flow of the hydrogen sulfide gas to the vessel is stopped.

Creating a reference standard for hydrogen sulfide concentrations in crude oil can include using a piston cylinder sampling chamber in conjunction with the vessel. The piston cylinder sampling chamber can be attached to the vessel. The hydrogen sulfide gas-crude oil mixture can be drawn into the piston cylinder sampling chamber from the vessel before the piston cylinder sampling chamber is sealed and removed from the vessel.

In one aspect, creating a reference standard for hydrogen sulfide concentrations in crude oil includes: receiving a volume of crude oil in a vessel; flowing a hydrogen sulfide gas from a pressurized gas cylinder to the vessel to form a hydrogen sulfide gas-crude oil mixture; continuing flowing the hydrogen sulfide gas from the pressurized gas cylinder to the vessel at a set pressure for a predetermined time to adjust the hydrogen sulfide concentration in the hydrogen sulfide gas-crude oil mixture to a hydrogen sulfide threshold concentration; and stopping flow of the hydrogen sulfide gas to the vessel.

In some embodiments, raising the hydrogen sulfide concentration in the hydrogen sulfide gas-crude oil mixture to the hydrogen sulfide threshold concentration includes maintaining the pressure of the hydrogen sulfide gas-crude oil mixture between 3 psig and 7 psig.

In some embodiments, creating the reference standard for hydrogen sulfide concentrations in crude oil includes: attaching a piston cylinder sampling chamber to the vessel; flowing the hydrogen sulfide gas-crude oil mixture to the piston cylinder sampling chamber; sealing the piston cylinder sampling chamber; and removing the piston cylinder sampling chamber from the vessel. In some cases, creating the reference standard for hydrogen sulfide concentrations in crude oil includes maintaining the piston cylinder sampling chamber at between 3 and 7 psig.

In some embodiments, a purity of the hydrogen sulfide gas in the pressurized gas cylinder is at least 99%.

In some embodiments, the hydrogen sulfide threshold concentration is between 5 ppm and 70 ppm.

In some embodiments, the set pressure is between 3 psig and 7 psig. In some cases, the set pressure is 5 psig.

In some embodiments, the predetermined time is between 3 and 5 minutes. In some cases, the predetermined time is 5 minutes.

In some embodiments, the volume of the crude oil is between 300 mL and 600 mL.

In another aspect, a system for creating a reference standard for hydrogen sulfide concentrations in crude oil includes: a vessel comprising an inlet and an outlet; a pressurized cylinder containing a hydrogen sulfide gas, the pressurized cylinder connected to the inlet of the vessel to flow the hydrogen sulfide gas from the pressurized cylinder to the vessel at a set pressure for a predetermined time; a control valve positioned in between the inlet of the vessel and the pressurized cylinder to control the flow of the hydrogen sulfide gas from the pressurized cylinder to the vessel; and a piston cylinder sampling chamber connected to the outlet of the vessel.

In some embodiments, a purity of the hydrogen sulfide gas in the pressurized gas cylinder is at least 99%.

In some embodiments, the system for creating the reference standard for hydrogen sulfide concentrations in crude oil further includes a pressure gauge connected to the vessel.

In some embodiments, a volume of the vessel is between 700 mL and 800 mL. In some cases, the volume of the vessel is 750 mL.

In another aspect, a method for creating a reference standard for a gas phase of a compound dissolved in crude oil includes: receiving a crude oil containing a gas phase of a compound dissolved in crude oil in a vessel; flowing a gas phase of the compound from a pressurized gas cylinder to the vessel to form a gas compound-crude oil mixture; continuing flowing the gas phase of the compound from the pressurized gas cylinder to the vessel at a set pressure for a predetermined time to adjust a gas concentration of the compound-crude oil mixture to a gas threshold concentration; and stopping flow of the gas phase of the compound to the vessel.

In some embodiments, the method for creating the reference standard for the gas phase of the compound dissolved in crude oil further includes: attaching a piston cylinder sampling chamber to the vessel; flowing the gas compound-crude oil mixture to the piston cylinder sampling chamber; sealing the piston cylinder sampling chamber; and removing the piston cylinder sampling chamber from the vessel.

In some embodiments, a volume of the crude oil is between 300 and 600 mL and the gas threshold concentration is between 5 ppm and 70 ppm.

In some embodiments, the set pressure is between 3 psig and 7 psig and the predetermined time is between 3 minutes and 5 minutes.

Implementations of the present disclosure can realize one or more of the following advantages. These systems and methods can be used to create a reference standard for a gas at low concentrations in crude oil. For example, a reference standard for hydrogen sulfide gas at 5 ppm to 70 ppm in Arab light crude oil can be formed. A reference standard for a gas at low concentrations in crude oil can confirm proper operation of test instruments. A reference standard containing a pressurized gas can be maintained for test instrument operation checks at different geographic locations.

The details of one or more implementations of the subject matter described in this disclosure are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
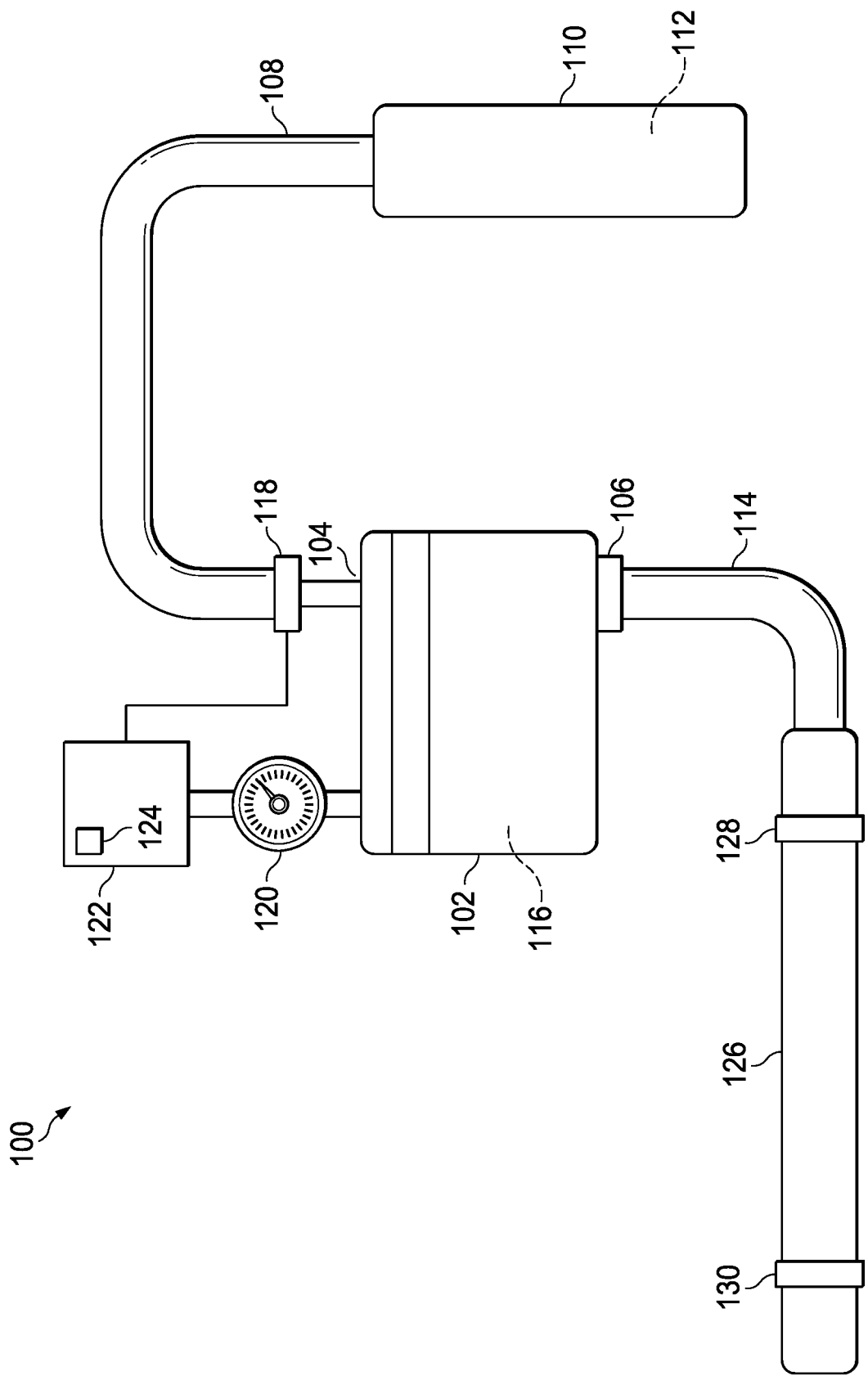
FIG. 1 is a schematic view of a system for creating a crude oil reference standard.

The present disclosure relates to creating crude oil reference standards.

Monitoring crude oil quality (conditions and properties) is a critical aspect of upstream oil and gas production operations. Crude oil is treated, through a variety of processes, to meet various standards. Timely and reliable monitoring of the data is critical for rigorous quality control prior to shipping the crude oil to a downstream refining operation or a consumer. Monitoring crude oil quality is also used for process optimization, process troubleshooting, system performance checks, and personnel safety. Crude oil quality can be monitored by test instruments positioned at different geographic locations. For example, the quality of the crude oil can be monitored at well sites, pipelines, laboratories, refineries, and distribution terminals. Some crude oil properties than can be measured are water content, salt concentration, concentrations of dissolved gasses (e.g., hydrogen sulfide), and vapor pressure (VPCR). Proper operation of the test instruments for measuring the gas concentration in a sample of crude oil is verified by operating the test instruments to measure a reference standard sample with a known gas concentration.

These systems and methods provide an approach to creating crude oil reference standards for compounds that may be naturally present in the crude oil of interest. For example, dissolved hydrogen sulfide ($H_2S$) is sometimes present in crude oil from some fields in the Middle East. Exposing a sample of the crude oil to gas phase hydrogen sulfide at a set pressure and temperature for a set period of time can provide a controlled concentration of dissolved hydrogen sulfide in the sample. The initial sample of crude oil is first cleaned by bubbling the initial sample of crude oil with nitrogen gas to ensure the dissolved hydrogen sulfide concentration is less than 1 ppm. This avoids the requirement of an initially clean solvent in approaches that provide a reference standard by cleaning and then spiking a known volume of solvent with a known volume of a compound of interest.

A reference standard for gas concentrations in crude oil is created by receiving a volume of crude oil containing a concentration of the gas in a vessel. A gas is flowed from a pressurized gas cylinder to the vessel to form a gas-crude oil mixture. The gas continues to flow from the pressurized gas cylinder to the vessel at a set pressure for a predetermined time to adjust the gas concentration in the gas-crude oil mixture to a gas threshold concentration. Once the gas concentration in the gas-crude oil mixture is at the gas threshold concentration, the flow the gas to the vessel is stopped.

Creating a reference standard for gas concentrations in crude oil can include using a piston cylinder sampling chamber in conjunction with the vessel. The piston cylinder sampling chamber can be attached to the vessel. The gas-crude oil mixture can be drawn into to the piston cylinder sampling chamber from the vessel before the piston cylinder sampling chamber is sealed and removed from the vessel.

For example, a reference standard for hydrogen sulfide concentrations in crude oil can be formed by receiving a volume of crude oil containing hydrogen sulfide at a concentration less than 1 ppm in a vessel. A hydrogen sulfide gas is flowed from a pressurized gas cylinder to the vessel to form a hydrogen sulfide gas-crude oil mixture. The hydrogen sulfide gas continues to flow from the pressurized gas cylinder to the vessel at a set pressure for a predetermined time to adjust the hydrogen sulfide concentration in the hydrogen sulfide gas-crude oil mixture to a hydrogen sulfide threshold concentration. After the predetermined time, the flow the hydrogen sulfide gas to the vessel is stopped.

Creating a reference standard for hydrogen sulfide concentrations in crude oil can include using a piston cylinder sampling chamber in conjunction with the vessel. The piston cylinder sampling chamber is a pressure vessel with an inlet valve, an outlet valve, and a piston to draw a portion of the hydrogen sulfide gas-crude oil mixture from the vessel into pressure vessel of the piston cylinder sampling chamber. The piston cylinder sampling chamber can be attached to the vessel. The hydrogen sulfide gas-crude oil mixture can be drawn into piston cylinder sampling chamber. The piston cylinder sampling chamber can be sealed and removed from the vessel. The piston cylinder sampling chamber can maintain the pressure of the hydrogen sulfide gas-crude oil mixture to keep the hydrogen sulfide gas in solution.

In some implementations of the present disclosure, a system forms a reference standard for hydrogen sulfide concentrations in crude oil. The system has a vessel with an inlet and an outlet. The vessel is filled with a crude oil containing hydrogen sulfide. A pressurized cylinder containing a hydrogen sulfide gas is connected to the inlet of the vessel to flow the hydrogen sulfide gas from the pressurized cylinder to the vessel at a set pressure for a predetermined time. A control valve is positioned in between the inlet of the vessel and the pressurized cylinder to control the flow of the hydrogen sulfide gas from the pressurized cylinder to the vessel. A piston cylinder sampling chamber connected to the outlet of the vessel.

FIG. 1 is a schematic view of a system 100 for creating a crude oil reference standard. The system 100 has a vessel 102 as well as a pressurized cylinder 110 and a piston cylinder sampling chamber 126 attached to the vessel 102. As shown in FIG. 1, the vessel 102 has an inlet 104 and an outlet 106. In use, the vessel 102 can be filled with a crude oil containing a dissolved gas to be analyzed (e.g., hydrogen sulfide).

In system 100, the vessel 102 is an autoclave. In some systems, the vessel 102 can be also be a pressure vessel or a pressure reactor. The vessel 102 can safely contain the crude oil when the crude oil is pressurized and/or when the dissolved gas contained in the crude oil is a hazardous gas (such as hydrogen sulfide). The vessel 102 is constructed from metal to contain the chemicals in the crude oil, especially corrosive chemicals such as hydrogen sulfide. For example, the vessel 102 can be made of steel, a stainless steel, an alloy, or a super alloy.

A volume of the vessel 102 can be between 700 mL and 800 mL. For example, the volume of the vessel can be 750 mL. Different volumes of the vessel 102 may be used, however other test parameters such as flow rates, pressures, and quantities may need to be adjusted to form the reference standard.

The crude oil can be an Arab Light crude oil. Alternatively, the reference standard can be formed from other types of crude oils or liquids. The crude oil contains the hydrogen sulfide gas at an initial concentration of less than one ppm. A volume of the crude oil in the vessel 102 can be between 300 mL and 600 mL. The volume of the test standard may be used multiple times, that is to benchmark two or more laboratory test equipment's performance while maintaining the quality and specifications of the test standard. For example, between six and twelve tests may be conducted with a single reference standard formed by the methods described here with a volume between 300 mL and 750 mL.

The pressurized cylinder 110 is connected to the inlet 104 of the vessel 102. The pressurized cylinder 110 contains a gas 112 (e.g., $H_2S$) and is connected to the vessel 102 to flow the gas 112 from the pressurized cylinder 110 to the vessel 102 at a set pressure for a predetermined time. The gas 112 can be pressurized. For example, the pressure of the pressurized cylinder 110 can be between 5 psig and 250 psig. A purity of the hydrogen sulfide gas 112 is at least 99%. A conduit 108 connects the pressurized cylinder 110 to the vessel 102. The pressurized hydrogen sulfide gas 112 flows through the conduit 108.

The system 100 has a control valve 118 positioned in the conduit 108 in between the inlet 104 of the vessel 102 and the pressurized cylinder 110. The control valve 118 controls the flow of the hydrogen sulfide gas 112 from the pressurized cylinder 110 to the vessel 102. For example, the control valve 118 can be a pressure regulating valve to reduce a pressure of the pressurized cylinder 110 to the set pressure. For example, the control valve 118 can be a needle valve to regulate the flow of the hydrogen sulfide gas 112 from the pressurized cylinder 110 to the vessel 102 or a pressure regulator.

The system has a pressure gauge 120 connected to the vessel 102. The pressure gauge 120 senses a pressure of the hydrogen sulfide gas-crude oil mixture 116 in the vessel 102.

The system 100 can include a controller 122 to operate the control valve 118 to control the set pressure and predetermined time. The controller 122 can include a processor 124, that is, a computer with a microprocessor. The controller 122 has one or more sets of programmed instructions stored in a memory or other non-transitory computer-readable media that stores data (e.g., connected with the printed circuit board), which can be accessed and processed by a microprocessor. The programmed instructions can include, for example, instructions for sending or receiving signals and commands to operate the control valve 118 and/or collect and store data from the pressure gauge 120. The controller 122 stores values (signals and commands) against which sensed values (signals and commands) representing the pressure of the vessel 102 are measured. The processor 124 can generate a command signal to actuate the control valve 118 based on the predetermined time and the set pressure.

The system 100 can include a piston cylinder sampling chamber 126 connected to the outlet 106 of the vessel 102. The piston cylinder sampling chamber 126 receives the hydrogen sulfide gas-crude oil mixture 116 with the hydrogen sulfide gas at the hydrogen sulfide threshold concentration and maintains the hydrogen sulfide gas-crude oil mixture 116 with the hydrogen sulfide gas at the hydrogen sulfide threshold concentration at the set pressure for transportation from a preparation site (a laboratory) to a test site.

The piston cylinder sampling chamber 126 is optionally attached to the vessel 102. Another conduit 114 connects the piston cylinder sampling chamber 126 to the vessel 102. The piston cylinder sampling chamber 126 has an inlet valve 128 and an outlet valve 130. The inlet valve 128 and the outlet valve 130 control a flow of fluid into and out of the piston cylinder sampling chamber 126. For example, the inlet valve 128 controls the flow of the hydrogen sulfide gas-crude oil mixture 116 with the hydrogen sulfide gas at the hydrogen sulfide threshold concentration at the set pressure into the piston cylinder sampling chamber 126 at the preparation site. The piston cylinder sampling chamber 126 is then sealed by shutting the inlet valve 128 and disconnected (removed) from the vessel 102. The piston cylinder sampling chamber 126 maintains the hydrogen sulfide gas-crude oil mixture 116 with the hydrogen sulfide gas at the hydrogen sulfide threshold concentration at the set pressure at between 3 psig and 7 psig. For example, the pressure at which the piston cylinder sampling chamber maintains the set pressure can be 5 psig. The piston cylinder sampling chamber 126 is then transported to the test site where a portion of the hydrogen sulfide gas-crude oil mixture 116 is taken from the piston cylinder sampling chamber 126. The hydrogen sulfide gas-crude oil mixture 116 is removed by opening the outlet valve 130 which also controls flow of the hydrogen sulfide gas-crude oil mixture 116 with the hydrogen sulfide gas at the hydrogen sulfide threshold concentration at the set pressure into the test instrument. The test instrument is then calibrated against the known concentration of hydrogen sulfide.

The piston cylinder sampling chamber 126 can be a metal. For example, the piston cylinder sampling chamber can be steel, steel alloy, or titanium. The piston cylinder sampling chamber 126 can have a mixing ball (not shown). The mixing ball can move within the piston cylinder sampling chamber 126 to mix the contents (i.e., the test standard) during transportation. The piston cylinder sampling chamber 126 can have a volume between 0.5 L and 1.5 L. In some cases, the volume of the piston cylinder sampling chamber 126 is 640 mL or 1 L.

Before the piston cylinder sampling chamber 126 is connected to the vessel 102, it can be pre-charged by vacuuming the piston cylinder sampling chamber 126, that is, a vacuum is drawn in the piston cylinder sampling chamber 126. With the outlet valve 130 shut, the inlet valve 128 is opened, and the contents of the vessel 102 can be pushed from the vessel 102 into the piston cylinder sampling chamber 126. The inlet valve 128 is then shut and the piston cylinder sampling chamber 126 is disconnected from the vessel 102. The piston cylinder sampling chamber 126 containing the test standard (the hydrogen gas-crude oil mixture 116) can then be safely transported to another lab for analysis and testing.

Flowing the hydrogen sulfide gas 112 from the pressurized cylinder 110 at the set pressure and the predetermined time into the crude oil with the initial concentration of hydrogen sulfide gas forms a hydrogen sulfide gas-crude oil mixture 116 with the hydrogen sulfide gas at a hydrogen sulfide threshold concentration. The hydrogen sulfide threshold concentration can be between 5 ppm and 70 ppm. After the predetermined time, the hydrogen sulfide gas-crude oil mixture 116 can be used as a reference standard to verify proper operation of the test instruments.

The set pressure can be between 3 psig and 7 psig. For example, in some implementations, the set pressure can be 5 psig.

The predetermined time is between 3 minutes and 5 minutes. For example, in some implementations, the predetermined time is 5 minutes.

The set pressures, predetermined times, and hydrogen sulfide concentrations were developed by experiments. The objective of the experiments was to produce reproducible samples with $H_2S$ concentrations in the range of 5 to 70 ppm. A treated Arab Light crude oil sample was tested first to confirm a $H_2S$ concentration of less than 1 ppm. Next, pure $H_2S$ was injected through the crude oil in an autoclave at ambient temperature (23° C.). The autoclave volume, the $H_2S$ flow rate, and the contact time were the three parameters adjusted to control the spiked $H_2S$ concentrations.

The resulted crude oil sample was then stored in a piston cylinder to capture the Arab Light crude oil with a controlled $H_2S$ concentration in the sample before testing. Some test run data is listed in Table 1.

TABLE 1

Selected experimental conditions and final $H_2S$ concentration.

| Test Number | Arab Light Crude Oil Volume (mL) | $H_2S$ Pressure (psi) | Contact Time (min) | Final $H_2S$ Concentration (ppm) |
|---|---|---|---|---|
| 1 | 300 | 50 | 30 | 1786 |
| 2 | | 20 | 15 | 2300 |
| 3 | | 25 | 10 | 1699 |
| 4 | | 5 | 10 | 285 |
| 5 | | 5 | 5 | 177 |
| 6 | 600 | 5 | 5 | 38 |

These preliminary results suggested that by flowing pure $H_2S$ gas at 5 psi for 5 minutes into the 600 mL autoclave, a final $H_2S$ concentration would be within the desired range (5 ppm to 70 ppm). Additional tests were performed using the same parameters and consistent results were obtained as shown in Table 2.

TABLE 2

$H_2S$ spiked samples repeatability.

| Cylinder | Test Run # | Final $H_2S$ Conc. (ppm) | Average | Standard Deviation |
|---|---|---|---|---|
| #1 | 1 | 38 | 34.33 | 4.04 |

TABLE 2-continued $H_2S$ spiked samples repeatability.

| Cylinder | Test Run # | Final $H_2S$ Conc. (ppm) | Average | Standard Deviation |
|---|---|---|---|---|
| | 2 | 35 | | |
| | 3 | 30 | | |
| #2 | 4 | 37 | 34.05 | 2.64 |
| | 5 | 33 | | |
| | 6 | 32 | | |

Figure 2:
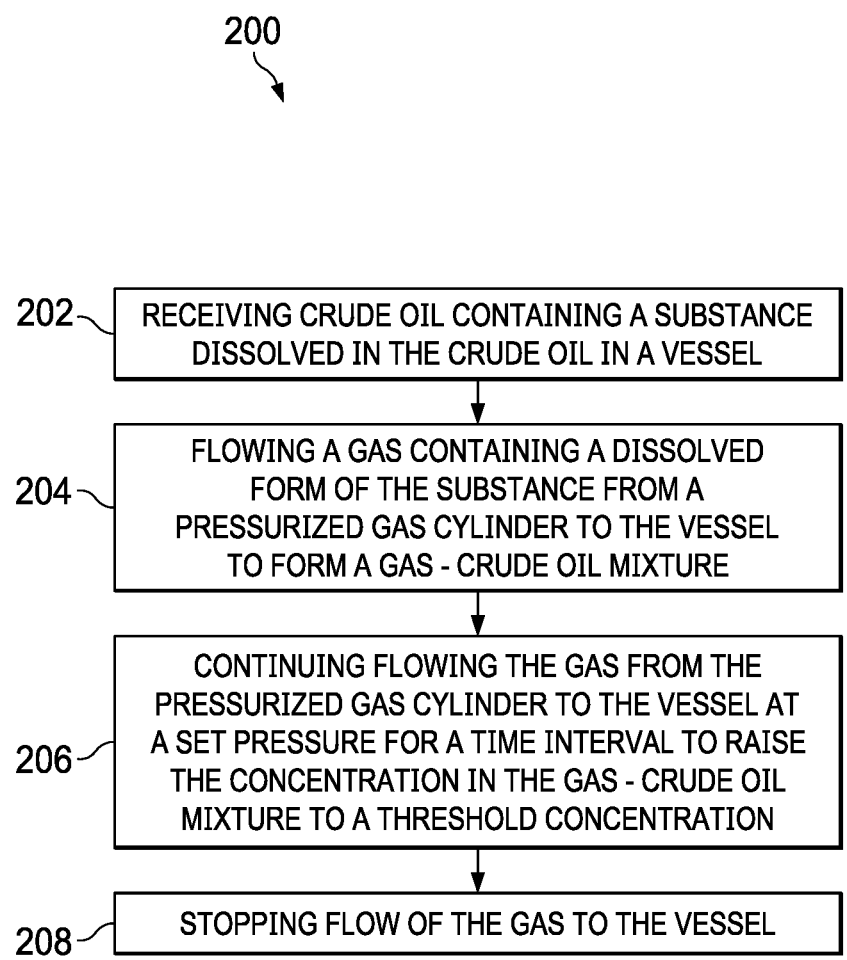
FIG. 2 is a flow chart of an example method of creating a crude oil reference standard according to the implementations of the present disclosure.

FIG. 2 is a flow chart 200 of an example method of creating a crude oil reference standard according to the implementations of the present disclosure. At 202, a volume of crude oil containing a dissolved gas is received in a vessel. The dissolved gas can be a hydrogen sulfide gas at a concentration of less than 1 ppm. The volume of the crude oil in the vessel can be between 300 mL and 600 mL. The initial hydrogen sulfide concentration can be less than a minimum detectable concentration. The initial hydrogen sulfide concentration can be reduced to less than 1 ppm by bubbling the crude oil with nitrogen gas. The crude oil sample with the hydrogen sulfide concentration less than 1 ppm can then be tested to verify the hydrogen sulfide concentration. The crude oil can be an Arab Light crude oil.

At 204, a hydrogen sulfide gas is flowed from a pressurized gas cylinder to the vessel to form a dissolved gas-crude oil mixture. A purity of the gas in the pressurized gas cylinder can be at least 99%. The pressurized cylinder 110 flows the hydrogen sulfide gas through the conduit 108 to the vessel 102. The control valve 118 controls the flow of the hydrogen sulfide gas from the pressurized cylinder 110 to the vessel 102. The control valve 118 can be opened fully or partially to allow the hydrogen sulfide gas to flow from the pressurized cylinder 110 to the vessel 102.

At 206, the hydrogen sulfide gas flow from the pressurized gas cylinder to the vessel at a set pressure for a predetermined time is continued to adjust the hydrogen sulfide concentration in the hydrogen sulfide gas-crude oil mixture to a hydrogen sulfide threshold concentration. The pressure of the hydrogen sulfide-crude oil mixture with the hydrogen sulfide concentration at the hydrogen sulfide threshold concentration can be maintained between 3 psig and 7 psig in the vessel.

The set pressure can be between 3 psig and 7 psig. In some cases, the set pressure is 5 psig. The predetermined time is between 3 minutes and 5 minutes. In some cases, the predetermined time is 5 minutes. In some cases, the hydrogen sulfide threshold concentration is between 5 ppm and 70 ppm.

At 208, the hydrogen sulfide gas flow to the vessel is stopped. The hydrogen sulfide gas flow can be stopped by shutting the control valve 118.

In some implementations, a piston cylinder sampling chamber collects the hydrogen sulfide gas-crude oil mixture with the hydrogen sulfide concentration at the hydrogen sulfide threshold concentration from the vessel. The piston cylinder sampling chamber is attached to the vessel. The hydrogen sulfide gas-crude oil mixture is drawn into the piston cylinder sampling chamber from the vessel before the piston cylinder sampling chamber is sealed. The piston cylinder sampling chamber is sealed and the piston cylinder sampling chamber is removed from the vessel. The piston cylinder sampling chamber can maintain the pressure of the hydrogen sulfide gas-crude oil mixture with the hydrogen sulfide concentration at the hydrogen sulfide threshold concentration at between 5 and 70 ppm.

In other implementations of the present disclosure, the system 100 can be can be used to create a reference standard in crude oil for simulating the exposure of a media to field conditions such as those found in an oil and gas well.

Although the following detailed description contains many specific details for purposes of illustration, it is understood that one of ordinary skill in the art will appreciate that many examples, variations, and alterations to the following details are within the scope and spirit of the disclosure. Accordingly, the example implementations described herein and provided in the appended figures are set forth without any loss of generality, and without imposing limitations on the claimed implementations.

Although the present implementations have been described in detail, it should be understood that various changes, substitutions, and alterations can be made hereupon without departing from the principle and scope of the disclosure. Accordingly, the scope of the present disclosure should be determined by the following claims and their appropriate legal equivalents.

The invention claimed is:

1. A method for creating a reference standard for hydrogen sulfide concentrations in crude oil, the method comprising:
    receiving a volume of crude oil in a vessel;
    flowing a hydrogen sulfide gas from a pressurized gas cylinder to the vessel to form a hydrogen sulfide gas-crude oil mixture;
    continuing flowing the hydrogen sulfide gas from the pressurized gas cylinder to the vessel at between 3 and 7 psig for between 3 and 5 minutes to adjust a hydrogen sulfide concentration in the hydrogen sulfide gas-crude oil mixture to a hydrogen sulfide threshold concentration between 5 and 70 ppm; and
    stopping flow of the hydrogen sulfide gas to the vessel.

2. The method of claim 1, wherein raising the hydrogen sulfide concentration in the hydrogen sulfide gas-crude oil mixture to the hydrogen sulfide threshold concentration comprises maintaining a pressure of the hydrogen sulfide gas-crude oil mixture between 3 psig and 7 psig.

3. The method of claim 1, further comprising:
    attaching a piston cylinder sampling chamber to the vessel;
    flowing the hydrogen sulfide gas-crude oil mixture to the piston cylinder sampling chamber;
    sealing the piston cylinder sampling chamber; and
    removing the piston cylinder sampling chamber from the vessel.

4. The method of claim 3, further comprising maintaining the piston cylinder sampling chamber at between 3 psig and 7 psig.

5. The method of claim 1, wherein a purity of the hydrogen sulfide gas in the pressurized gas cylinder is at least 99%.

6. The method of claim 1, wherein continuing flowing the hydrogen sulfide gas from the pressurized gas cylinder to the vessel at between 3 and 7 psig comprises continuing flowing the hydrogen sulfide gas at 5 psig.

7. The method of claim 1, wherein continuing flowing the hydrogen sulfide gas from the pressurized gas cylinder to the vessel for between 3 and 5 minutes comprises continuing flowing the hydrogen sulfide gas for 5 minutes.

8. The method of claim 1, wherein the volume of the crude oil is between 300 mL and 600 mL.

* * * * *